United States Patent [19]

Krueger

[11] Patent Number: 5,437,201
[45] Date of Patent: Aug. 1, 1995

[54] NEGATIVE PRESSURE GAS SAMPLING DEVICE

[75] Inventor: Dennis C. Krueger, Richmond, Tex.

[73] Assignee: Shell Oil Company, Houston, Tex.

[21] Appl. No.: 221,288

[22] Filed: Mar. 30, 1994

[51] Int. Cl.⁶ .............................................. G01N 1/24
[52] U.S. Cl. .................... 73/864.35; 73/863.84; 73/864.11; 73/864.62
[58] Field of Search ............ 73/23.41, 863.84, 863.86, 73/864.11, 864.13, 864.15, 864.16, 864.35, 864.62

[56] References Cited

U.S. PATENT DOCUMENTS

| | | | |
|---|---|---|---|
| 1,837,858 | 12/1931 | Grace | 73/863.84 |
| 2,223,785 | 12/1940 | Hassler | 23/257 |
| 2,767,587 | 10/1956 | Perkins | 73/863.86 |
| 2,982,134 | 5/1961 | Brown | 73/863.86 |
| 2,994,224 | 8/1961 | Brown | 73/863.84 |
| 2,995,931 | 8/1961 | Perry et al. | 73/863.84 |
| 3,463,357 | 8/1969 | MacLean, Jr. et al. | 73/863.86 |
| 3,736,099 | 5/1973 | Begg et al. | 73/864.11 |
| 3,793,887 | 2/1974 | Anderson et al. | 73/864.64 |
| 3,866,474 | 2/1975 | Hssselmann | 73/421.5 R |
| 3,950,136 | 4/1976 | Bellinga | 23/232 R |
| 3,965,946 | 6/1976 | D'Alo | 141/51 |
| 3,982,438 | 9/1976 | Byrd | 73/864.11 |
| 4,009,617 | 3/1977 | Johnson | 73/863.84 |
| 4,269,064 | 5/1981 | Johnson et al. | 73/863.84 |
| 4,296,071 | 10/1981 | Weiss et al. | 73/864.11 |
| 4,381,408 | 4/1983 | Rounbehler et al. | 564/112 |
| 4,437,346 | 3/1984 | Kummer | 73/863.86 |
| 4,440,032 | 4/1984 | Welker | 73/863.84 |
| 4,525,127 | 6/1985 | Welker | 73/863.84 |
| 4,527,437 | 7/1985 | Wells | 73/864.16 |
| 4,580,452 | 4/1986 | Masson | 73/863.86 |
| 4,628,750 | 12/1986 | Welker | 73/864.62 |
| 4,631,483 | 12/1986 | Proni et al. | 73/864.11 |
| 4,635,487 | 1/1987 | Gowing | 73/864.62 |
| 4,858,478 | 8/1989 | Kush et al. | 73/864.62 |
| 4,947,696 | 8/1990 | Fehlauer | 73/863.84 |
| 4,984,476 | 2/1991 | Dahrendorf et al. | 73/864.35 |
| 5,174,163 | 12/1992 | Gussman et al. | 73/864.62 |

OTHER PUBLICATIONS

Advertisement: "10-Liter Vacuum Bag Sampler," No. 912-0365, by Supelco, Division of Rohm and Haas, 2 pp. (1992).
Advertisement: "Automatic Six-Bag Sampler Collects Multiple Air Samples," No. 912-0361, by Division of Rohm and Haas, 2 pp. (1992).
Advertisement: "1-Liter Vacuum Bag Sampler," No. 912-0362, by Supelco, Division of Rohm and Haas, 2 pp. (1992).
Advertisement: "Whitney Ball Valves," W-371B, by Whitney Co., 318 Bishop Road, Highland Heights, Ohio 44143 (Copyright 1973-1984 Marked Service Co.).

Primary Examiner—Richard E. Chilcot, Jr.
Assistant Examiner—George M. Dombroske
Attorney, Agent, or Firm—Todd F. Volyn

[57] ABSTRACT

An apparatus for collecting fluid samples is presented having a sealable container which has an opening and a cover for sealing and unsealing the opening, an inlet which includes a means for communicating between the inside of the container and the environment outside the container, a sample vessel which has an orifice or other means for filling and sealing it when samples are drawn therein through the inlet, and a means for selectively evacuating and pressurizing the space between the vessel and the container. Actuation of the means for evacuating and pressurizing the space between the vessel and the container repeatedly induces the vessel to alternately be filled with fluid from the environment outside the container and emptied of its contents to the environment through the inlet. A fluid sampling method is also provided.

19 Claims, 3 Drawing Sheets

NEGATIVE PRESSURE GAS SAMPLING DEVICE

FIELD OF THE INVENTION

This invention relates to fluid sampling. More particularly this invention relates to fluid sampling for the detection of pollutants and contaminates.

BACKGROUND OF THE INVENTION

Environmental protection and health related issues have placed a special impetus on accurately taking samples from source emissions into the atmosphere, soil, and water. Analytes are typically tested at such low concentrations that even a small error in sampling can negate the validity of a sophisticated testing protocol. The design of collection vessels and devices used to fill those vessels contributes greatly to the validity of such procedures.

One vessel which has become widely accepted for use in this area is the "TEDLAR" bag (a tradename of the E. I. du Pont de Nemours Co., Inc.). In fact, it is presently the standard vessel for the sampling and analysis of source emissions. These bags have been found to be capable of collecting fluids containing any number of functional groups including hydrocarbons, halogenated organic moieties, alcohols, ketones, aldehydes, and aromatics. It is critical that the material used to collect and hold such samples not chemically react with the samples or matrix that contains the samples. This is generally the case with commercially available "TEDLAR" bags.

Selecting the appropriate sampling vessel also requires one to account for the proclivity of analyte to adsorb onto the vessel surface. This is predominantly a physical phenomena although it is not entirely divorced from the chemical reactivity of analyte and vessel surface. Analytes may adsorb onto the vessel surface by any number of well known phenomena and surface effects such as electrostatic attraction, London forces, etc. This is particularly troublesome where analyte concentration is low because some or all of the analyte may end up firmly affixed to the vessel surface. This could easily skew the results of an analysis of the vessel contents by several orders of magnitude.

Having decided upon the vessel to contain the sample, one next has to address how to collect and fill the vessel. This is a particularly important issue in ambient air monitoring where the analyte is in very small concentrations such as the low ppb (part per billion) range and cross contamination of sample is a concern. When the pressure of the fluid to be sampled is low, matters are further complicated by difficulties in transporting a fluid from a low pressure environment to a an environment at greater pressure.

One method adopted to overcome problems surrounding an awkward pressure gradient is through the employment of a negative pressure device. In such a device, a bag or other collapsible vessel is placed inside of an airtight container that has a passage way or conduit that connects the bag to the exterior of the container. The container is then evacuated by means of a pump. This induces a negative pressure or vacuum inside the container. The vessel is placed in communication with the environment from which one wishes to collect a sample. The vessel will fill with the sample as the pressure on both sides of the vessel equalize (provided the pressure inside the container is initially lower than the fluid pressure in the surrounding environment). U.S. Pat. No. 3,866,474 to Hasselmann is an example of such a device. It also incorporates an inert diluent gas.

While negative pressure sampling devices known in the art have solved many of the problems surrounding adverse pressure differentials, other difficulties continue to persist. In many cases, the only accurate or desirable place to sample fluid emissions is at their source. This is the case, for example, with many processes that vent byproduct or effluent through high velocity stacks. However, one who seeks to take a sample from such a stack will quickly realize that the negative pressure within the stack caused by rapidly exiting fluid makes negative pressure sampling very difficult. One must be able to create an intense vacuum within the container housing the sampling vessel to even fill the vessel. It would also be helpful if the device so employed was portable and remotable so that it could be placed in restrictive areas under harsh conditions. The device described in U.S. Pat. No. 3,866,474 for example, is only used to take samples at or near atmospheric pressure and is therefore inappropriate for use in this environment.

Another problem that is frequently encountered involves purging the sampling device and associated equipment of anything that is not sample. Generally, sampling devices have tubing, conduit, or other means of communicating between the inside of the vessel and the environment. This equipment is filled with air or whatever fluid the device is retained in. If an accurate sample is desired, this equipment and the contents of the vessel itself must first be purged of the surrounding fluid. This generally does not create a problem when the fluid purged or the sampling environment does not contain toxic or noxious contents. However, if this is not the case, those standing nearby can become exposed to danger when the sampling device is disconnected from the sampling line and its contents are purged. For example, it is not uncommon to place the inlet of a sampling device into an environment containing dangerous substances and fill the vessel. The inlet is then disconnected from the sampling line and it contents are purged into the same general environment in which the people taking the sample are found. When the vessel is completely purged it is then placed back onto the sampling line and a representative sample is collected. Obviously, this can be a dangerous undertaking.

Sampling an enclosed space which contains a limited quantity of fluid is also problematic with prior art methods. There are many instances in which one would like to withdraw a sample from such an environment without greatly disrupting the total pressure balance and fluid contents of that environment. Only the sample quantity is sought to be removed. This may be the case in certain environmental monitoring applications, off gassing of packaged products, and in applications such as in enclosed subterranean soil gas. If one were to employ prior art gas sampling methods they would introduce the inlet of a sampling device into the sampling environment and fill the vessel. The inlet is then removed from the sampling environment and the contents are expelled elsewhere while the lines of the device are purged. The inlet is then placed back into the sampling device and another sample is withdrawn. This can cause a tremendous pressure differential which can have a profound impact.

This type of problem can result in the structure surrounding the sampling environment giving way or in the introduction of outside air into the sampling environment where it would cause a dilution of that environment. For example, U.S. Pat. No. 2,223,785 to Hassler disclosed a device used to collect headspace samples from subterranean oil and gas deposits. The device therein disclosed and claimed would necessarily displace a greater volume of fluid from the deposit than was necessary due to purging and other aspects of its operation. If this device were used to sample soil gas in shallow ground water wells, atmospheric air could be drawn into the well while purging large volumes thus diluting the sample.

In the oil and chemical industry, it is often necessary to sample atmospheres in hazardous areas where explosive concentrations may be expected at all times, or where explosive conditions may be expected under abnormal conditions. These hazardous areas are classified as Class I, Division I and Class I, Division II areas respectively. Sampling in these areas could benefit from a device that does not require a source of electricity nearby, can take accurate samples without creating undue pressure gradients, and is compact and portable.

Some unique problems exist when the fluid being sampled is a liquid such as water as opposed to a gas or gaseous mixture such as air. Frequently the analyte that is to be sampled from the liquid is in a state of equilibrium which must be preserved to ensure that a portion of the sample is not lost to volatilization. This is critically important in the case of testing water for semi-volatile and volatile species. As long as the vapor pressure above a liquid is retained at the value that is found when the sample is in its unaltered state and the sample is not agitated while open to the atmosphere, a sample of liquid taken from an area to be tested will accurately reflect the contents of the analyte.

A common form of analysis when working with a liquid medium involves a gas analysis of the headspace of the liquid sample in an enclosed vial. One can determine the quantity of analyte in a liquid medium by measuring the concentration of the analyte above the liquid medium provided the medium and analyte are in equilibrium according to Henry's Law.

However, if one withdraws a liquid sample and agitates it by pouring it from the collection vessel into the analysis vessel, the resulting headspace of the sample (the space above the liquid) will change because the volatile analyte will lose its association with the liquid. Analyte and medium will come to an equilibrium in which an analysis of the headspace based upon Henry'-Law will give a value for the organic species dissolved in the water that is inaccurately low. Thus, a collection device which allows one to collect sample without exposing the sample to the atmosphere after collection has occurred would be helpful in the analysis of liquids.

The art of fluid sampling could greatly benefit by the introduction of a new method and device that would mitigate the effects of analyte adsorption, overcome the problems associated with sampling in a strongly pressure negative environment, enclosed spaces, allow collection in hazardous atmospheres, and allow collection in liquid media. It would be particularly desirable if such a device and method would allow one to take a sample where analyte concentrations are small without the problems that accompany prior art methods.

SUMMARY OF THE INVENTION

It is an object of this invention to provide an apparatus that allows small quantities of analyte to be sampled from a variety of fluid sample environments to include air and water.

It is a further object of this invention to provide a fluid sampling apparatus that can be used in conjunction with commonly available and accepted sampling vessels such as the "TEDLAR" bag.

It is a yet further object of this invention to provide a fluid sampling apparatus which permits a sample to be withdrawn without contacting any part of the apparatus apart from the interior of the sampling vessel and the means for communicating between the sample environment and the interior of the sampling vessel.

It is a yet further object of this invention to provide a fluid sampling apparatus that mitigates the effect of analyte adsorption on sample vessel surfaces.

It is a yet further object of this invention to provide a portable fluid sampling apparatus that can be carried by the average person and can yet overcome the effects of sampling in negative pressure environments such as those encountered in industrial stacks, vents, and lines under vacuum.

It is a yet further object of this invention to provide a method for sampling a fluid such that small quantities of analyte can be accurately assayed from the sample.

In accordance with these and other objects of this invention an apparatus for collecting fluid samples is presented comprising:

- a sealable container having an opening and a cover for sealing and unsealing the opening;
- an inlet which includes a means for communicating between the inside of the container and the environment outside the container;
- a sample vessel which has an orifice or other means for filling and sealing it when samples are drawn therein through the inlet; and
- a means for selectively evacuating and pressurizing the space between the vessel and the container;
- actuation of the means for evacuating and pressurizing the space between the vessel and the container thereby repeatedly induces the vessel to alternately be filled with fluid from the environment outside the container and emptied of its contents to the environment through the inlet.

The sampling apparatus is said to bellows. This can be done through manual means, electro-mechanical means, or automated means.

A fluid sampling method is also provided comprising: placing a sample collection means within a rigid sealable container, selectively evacuating the space between the collection means and the container; actuating a communication means between the collection means and the sampling environment so that the collection means is substantially filled with fluid to be sampled; selectively pressurizing the space between the collection means and the container so the collection means is emptied of sample; selectively repeating the steps of filling and emptying the collection means and then sealing the filled collection means.

Both the method and apparatus can be used to sample liquid and gaseous analytes.

DETAILED DESCRIPTION OF THE INVENTION

A new device is presented for taking fluid samples. This new device mitigates sampling error due to analyte adsorption on the container media and interior of a pump chamber. It also allows samples to be taken from a pressure and volume sensitive environment without substantial disruption of that environment. The device can be fashioned as a system that is portable by the average person for field use and yet produces enough vacuum to be useful for taking samples in strongly pressure negative environments.

Figure 1:
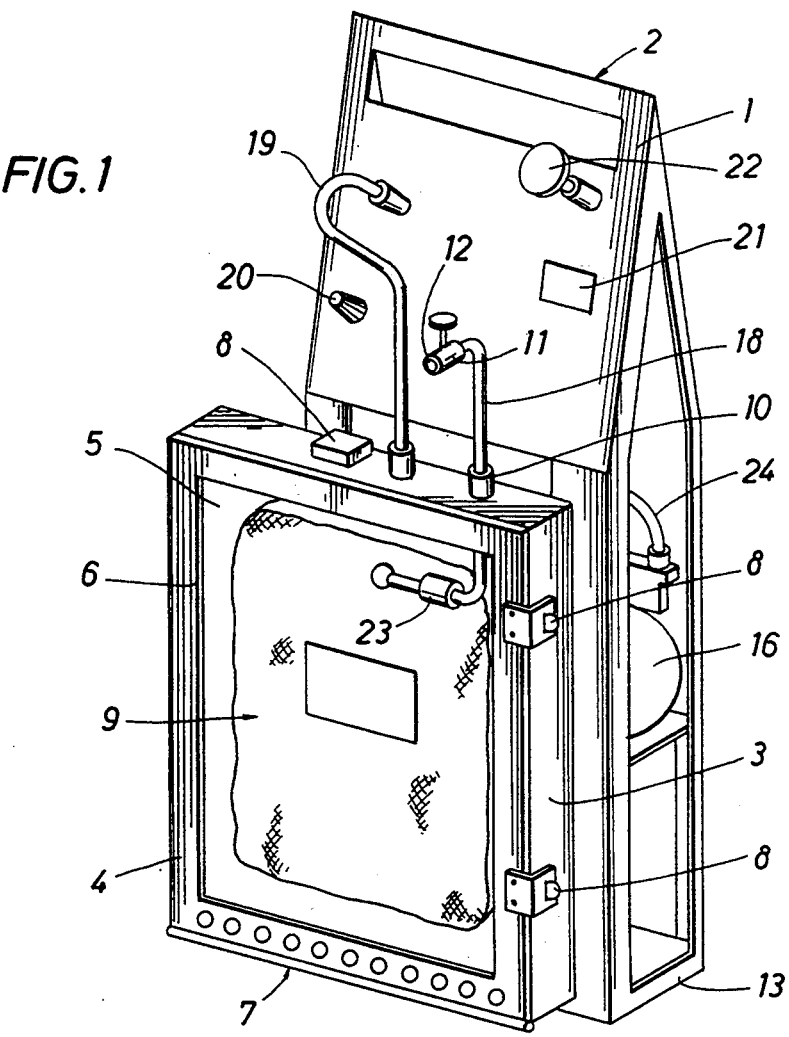
FIG. 1 is a front view of one embodiment of the apparatus for collecting fluid samples powered by an electrically actuated pump.

Turning now to the drawings, in FIG. 1 a housing 1 can be used to retain all of the components of the apparatus in a fixed relationship to each other. It may be fabricated from any rigid material such as aluminum or polyethylene. Since many applications make it desirable to have a rugged yet portable sampling device aluminum is generally preferable. The housing 1 may be fashioned to intrinsically incorporate a handle 2 by constructing it so that the lower portion of the housing is box- like and the upper portion defines a pyramid with its base being a rectangle conforming to the upper surface of the lower portion. In this way, the apex of the pyramid can serve as a handle. The apex handle and essentially vertical construction of the frame of the preferred embodiment contributes to the ability to easily pull the device up a caged ladder by a rope or cable.

Sealable, rigid-walled container 3 is detachably affixed to the front portion of housing 1. The housing may be construed as merely supplying a means for transporting the container and keeping it in a fixed relationship to the other components of the apparatus. The container can also be detached so that it may be operated remotely and used in confined areas. For example, the container may be connected to the pump apparatus by a length of tubing. This container 3 is attached by an "L" shaped clip but any detachable fastening device such as machine screws or nuts and bolts can be used to affect this construction. It is also possible to remove the container completely and use a syringe, connect it by means of a vacuum line to a remote vacuum pump, or other means for selectively evacuating the space therein to operate the apparatus.

The container 3 is best made of unitary construction as a box having one open surface. If necessary, the box shape may be attained by shaping a piece of aluminum or other suitable material and welding the seams to make it air tight. The front portion of the container is made from a rim 4 fabricated from the same or similar material as the remainder of the container. Glass or face 5 comprises the bulk of the front surface and is retained in place under a stiffening frame, 6. Of course, any suitable substitute for glass such as polymethylmethacrylate can be used provided it will not break or crack under a strong negative pressure and is stiffened and made rigid. This may be done, for example, by affixing a frame around it. While a transparent surface is desirable, it is also possible to have an opaque or translucent face. If this is the case, then it is desirable to have a sensor inside the container to signal when the collection vessel is full.

The face, 5 is fixed to a side of the container by means of one or more air tight hinges, 7. In a preferred embodiment, hinge, 7 is a piano hinge. Fasteners 8 hold the front surface in the closed position so that the container can be sealed. The preferred embodiment uses cam-actuated fasteners for this purpose.

A removable flexible fluid sample vessel 9 is used to collect sample, it will be understood by those skilled in the art that container 3 need not be restricted to any particular shape or dimension. However, the inner dimensions of the container should be greater than the outer dimensions of the vessel 9 when the vessel 9 is filled to its maximum capacity. In the preferred embodiment of this invention, the vessel is comprised of a "TEDLAR" bag. In other embodiments of this invention any flexible material that can be caused to be collapsed or expanded and thereby emptied of the contents of the vessel 9 are used. Such vessels will typically be sealable and have an orifice through which sample may be injected or deposited. Of course, upon filling a vessel with the appropriate amount of sample, the orifice must be made to close. Generally, the orifice will also be capable of being reopened so that sample may be withdrawn from the vessel for subsequent assay. The material comprising the sample vessel should be chosen so that it is inert to the analyte to be assayed.

In the preferred embodiment of the invention, a $\frac{1}{4}''$ "SWAGELOK" (a tradename of Swagelok Co.) brand bulkhead compression union, 10 is used to bridge the wall of the container. A small section of $\frac{1}{4}''$ O.D. diameter "TEFLON" brand tubing (a tradename of E. I. du Pont de Nemours and Co., Inc.), 23 extends through the union and into the container, 3. The valve stem of the tedlar bag (containment vessel, 9) forms a friction fit seal with the interior of the "TEFLON" brand tubing.

Inlet, 18 functions as a means for conducting the sample from the sampling environment, through the wall of the rigid container, to the inside of the flexible sample collection vessel. In this way, sample and analyte do not contact portions of pumps or other mechanical means as the sample proceeds to the interior portion of the collection vessel. This avoids contamination of sample and subsequent samples that would otherwise also pass through such components of the device. Sample enters the device through the end connection, 12 of valve, 11.

Valve, 11 is placed between the sample source and the collection vessel on the exterior of the rigid container. Valve, 11 allows the collection vessel to be sealed while the interior of the rigid container returns to atmospheric pressure at the end of the sampling run. This then allows the door to be opened without sample being sucked back into a negative pressure environment such as in a high velocity stack or vacuum line. Needle valve, 22 can also be used to control the rate of evacuation or pressurization of container, 3.

It will be readily appreciated by those skilled in the art that the inlet, 18 is in communication with vessel, 9 such that sample does not unnecessarily pass through any other portion of the device. In this way, carryover from previous samples is avoided. That is, it avoids the problem of introducing analyte or contaminate that might linger in or adsorb onto mechanical components such as a pump chamber.

A tight seal is afforded between the front surface and the outer edge of the rest of container 3 by a sealing means which is placed at a point of contact all along the interface between these surfaces. In a preferred embodiment, a ½" lip is formed around the perimeter of the container for this purpose. This sealing means may be comprised of a gasket, polymeric substance, or through the use of other commonly used methods for sealing surfaces that are in contact with each other. Finely machining the contacting surfaces is another way to afford such a tight seal although this is not generally preferred.

The preferred embodiment of this invention is capable of inducing a vacuum in container, 3 of five inches Hg. This level of vacuum enables the device of the instant invention to pull a sample from most stacks since most stacks operate at less than three inches of Hg. For many applications, however, a much lesser vacuum will suffice. Thus, it will be understood that any amount of vacuum sufficient to evacuate the container and the vessel held within the container is within the scope of this invention.

Figure 2:
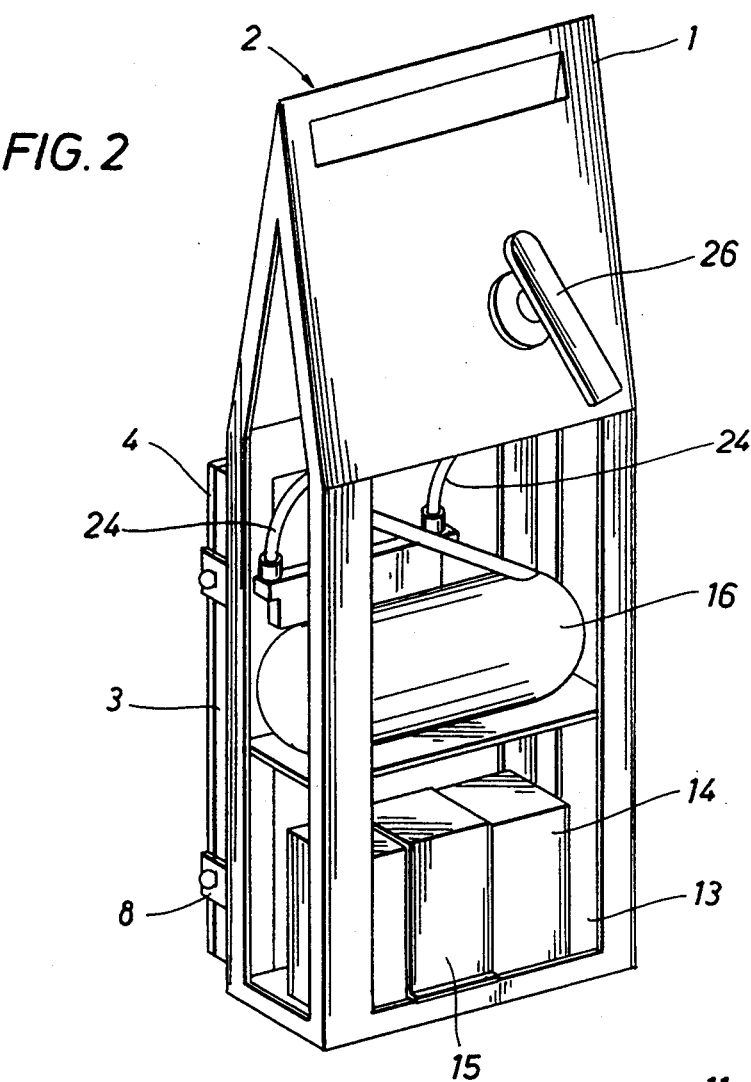
FIG. 2 is a view of the back of the embodiment of the apparatus shown in FIG. 1.

FIG. 2 shows that a base 13 supports a battery 14 which is fastened in place by fastener 15. Fasteners, 15 are preferably strap fasteners. It will be understood by those skilled in the art that any source of electrical or mechanical power that can drive a pump can be used here. For example, it is also possible to power the embodiment of this invention which employs an electrical pump from a source of electricity which is external to the apparatus. In such a case, the battery operated DC pump can be replaced with an AC operated pump that is outfitted with a receptacle for plugging into a standard source 112 volt power line. For convenience and portability, a 12 volt battery may be used and is incorporated in the preferred embodiment of this invention.

Figure 5:
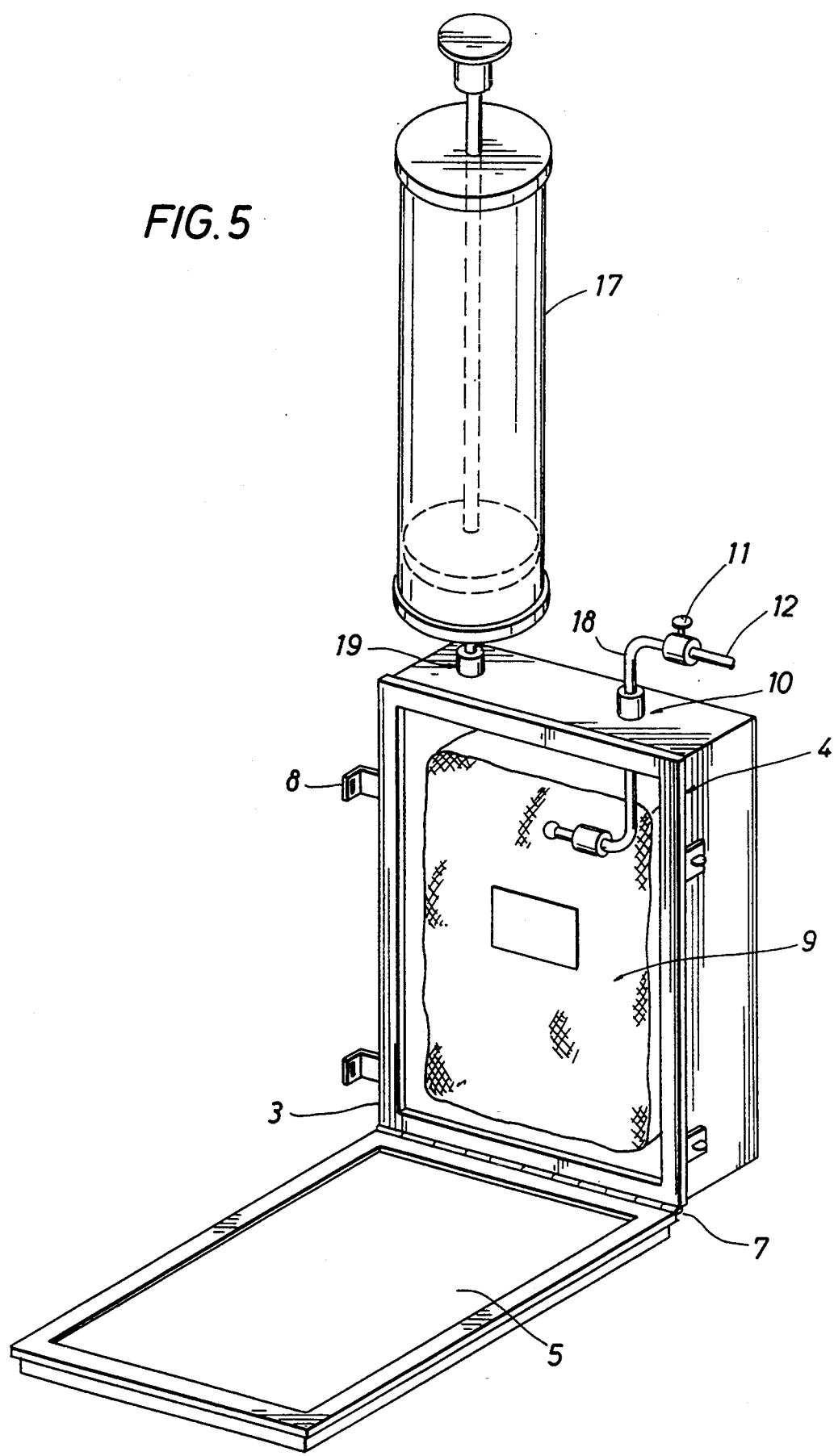
FIG. 5 is a view showing both the front and sides of an embodiment of the sealable rigid-walled container that serves as the apparatus for manually collecting fluid samples using the method claimed.

Battery 14 supplies power to pump 16. In the embodiment of the invention shown in FIG. 1 which is the preferred embodiment of this invention, pump 16 serves as a means for selectively evacuating or pressurizing the space between the inner surfaces of container 3 and the outer surfaces of the sampling vessel 9. A syringe or other device capable of inducing negative and positive pressures can also be used in this capacity. FIG. 5 shows syringe 17 for use as an alternative embodiment in the method of this invention. The means for selectively evacuating or pressurizing the space is in communication with the inner portion of the container 3 by its replacement of valve connection 19.

The pump, 16 is preferably connected to the container, 3 by conduit, 24. The pump, 16 which can be actuated by on/off switch, 21, has a further inlet/outlet, 20 for suction and exhaust.

The preferred embodiment of this invention employs a four way valve, 25 (shown schematically in FIGS. 3 and 4) as a switching device to change pump direction and allow container 3 to be either pressurized or evacuated. Four way valve 25 is placed in a convenient location on the housing 1 between the pump, 16 and the container, 3. The "SS-43YF2" 4-way ball valve manufactured by Whitey Company of Highland Heights, Ohio is the preferred four way valve for this purpose. However, it will be understood that any switching device (such as three way switching valves) which enables the pump, 16 (or other means for selectively evacuating and pressurizing the space to be reversed) can be used.

Preferred switching devices are capable of causing a transition in the direction of the pump to occur within one second. It is also preferred that the switching device be capable of repeated and rapid changes in direction as will be explained in the Operations section below. This can be accomplished by the rotation of valve control, 26.

Figure 3:
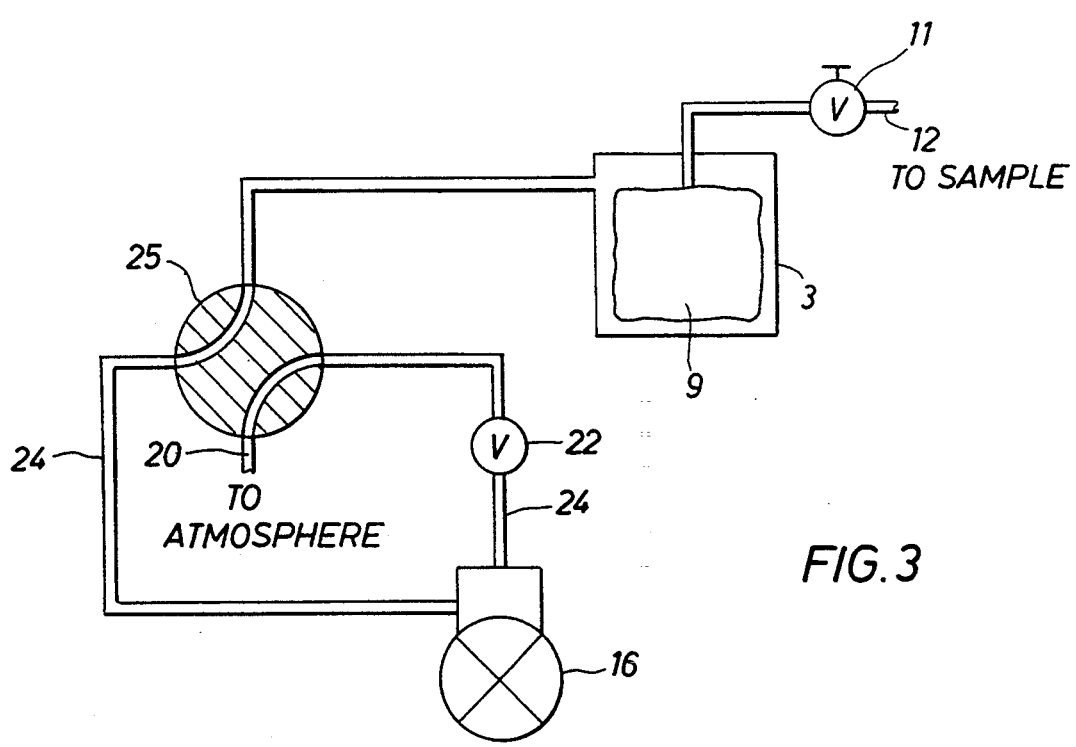
FIG. 3 is a schematic diagram showing the operation of an embodiment of the invention actuated by a pump and utilizing a four-way crossover valve.

FIG. 3 schematically illustrates the use of the preferred embodiment comprising a four-way valve. The valve, 25 shown here shows an open pathway between the pump 16 and the container, 3 in which the pump creates a vacuum in the container. The valve, 25 also allows the pump to exhaust its contents to the atmosphere. This can also be moderated by needle valve, 22. This action induces a negative pressure on sample vessel, 9. The sample vessel, 9 may be placed in communication with the environment by means of valve, 11 when this valve is placed in the open position sample and sample matrix fills the vessel, 9.

Figure 4:
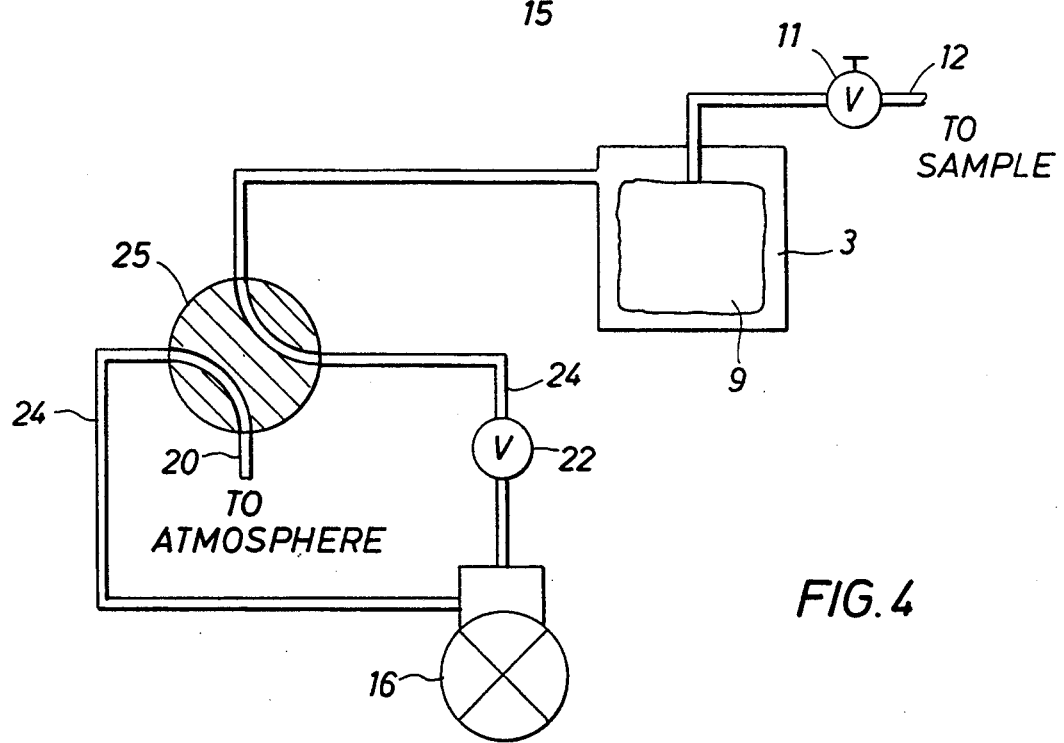
FIG. 4 is a schematic diagram showing the operation of an embodiment of the invention actuated by a pump and utilizing a four-way crossover valve.

FIG. 4 schematically illustrates the use of the preferred embodiment comprising a four-way valve when the valve position in FIG. 3 is rotated. In this figure, the valve 25 allows a pathway between the pump 16 and the container, 3 in which a positive pressure is induced therein. The pump withdraws air (or other fluid) from the atmosphere through the valve, 25 in this case. The amount of positive pressure introduced into the container, 3 can be moderated by needle valve, 22. This action induces a positive pressure on sample vessel, 9. The sample vessel, 9 may be emptied into the environment by means of valve, 11 when this valve is then placed in the open position.

FIG. 5 shows an embodiment of the instant invention wherein the means for selectively evacuating the container is manual. In this case, the container 3 is removed from housing 1 and is itself the apparatus. A syringe, 17 is affixed to valve connection, 19 thereby replacing valve, 25. This serves as a hand powered, reversible pump and can be used to evacuate and pressurize the interior of the container causing the bag to inflate and deflate. Preferred syringes include "S-1000" model 1 liter syringe and "S-1500" model 1.5 liter syringe manufactured by the Hamilton Company. However, any means that can enable one to manually evacuate and pressurize the container repetitively may be employed in this capacity.

Such a hand powered configuration is a light weight, portable device which can be advantageously used to collect samples from inside enclosed vessels or areas that contain Class I, Division I or II atmospheres. This avoids the danger of creating an explosion attendant with the use of an electrically powered pump. This same principle can be put to good use in withdrawing samples from inside tall reaction vessels and other confined spaces.

OPERATION

One may undertake the following procedures to fill the collection means with sample. The collection vessel is first attached to the container in such a manner that the inside of the collection vessel is in communication with a means for passing fluid from the outside environment containing the analyte through the container wall to the inside of the collection vessel. The front surface of the container is then closed so that the container is sealed.

The container is evacuated by means of a pump or syringe. This is done by introducing a vacuum in the space between the outer surface of the collecting means and the inner surface of the container.

Evacuation of the space between the collection vessel and the interior walls of the container causes the collection vessel to be placed in a negative pressure environment. When valve 11 is open, gas or liquid flows into the collection vessel in an effort to equalize the pressure on both sides of the container wall. The fluid is trapped in the collection vessel, which causes the collection vessel to expand. This is commonly achieved by using a standard "TEDLAR" bag or other sample collection bag known by those in the art.

When the collection vessel is substantially filled the pressure in the container is reversed. That is, a positive pressure with respect to the outside environment is induced in the container. In the preferred embodiment of the invention, this is achieved by rotating the crossover valve which reverses the direction of the pump flow and pressurizes the container with respect to the outside environment. This causes the fluid in the collection vessel to exit back into the sample environment. This process of alternately filling and emptying the vessel by reversing the pressure in the container is defined as bellowsing for the purposes of this specification. After one or more iterations of the bellowsing process the sample vessel is sealed by closing the valve, 11 and turning off the pump, 16.

Putting the valve, 11 in the closed position prevents collected sample from being drawn back into the sampling environment. The door to the rigid container is opened, the sealable portion on the orifice of the vessel is sealed (where the vessel is a "TEDLAR" brand bag, this is a shutoff valve), and the vessel is removed from the container.

The method of this invention and the apparatus that may be used to practice it use a bellowsing action to obtain accurate samples. Bellowsing may be done a number of times with the released contents of the vessel returned to the sample environment so that pressure differentials are not induced into the system from which the sample is taken. Thus, samples may be taken from a pressure sensitive environment or an environment that contains a limited volume of analyte without introducing undue or dangerous amounts of air or other gases into the sample environment from another source. It is also possible to accurately sample even very low concentrations of analyte in this manner. For example, samples have been taken from atmospheres having a volume of about ten (10) liters. It has been found that analyte concentrations between about 10 ppb and about 100 ppm are easily sampled using the instant method and apparatus. Generally, three iterations of bellowsing are used.

In another embodiment of this invention, the apparatus and method are controlled by a microprocessor programmed to alternately fill and empty the sample vessel a number of times in such a manner that sample integrity is optimized. In this embodiment of the invention the microprocessor may be programmed to be analyte specific so that vacuum strength, the number of bellowsing repetitions, and the rapidity of transition from filled to empty and empty to filled state are controlled. It will be understood by those skilled in the art that such controls and their equivalents can be programmed to adjust the operating parameters of this method and apparatus to adjust for any number of physical phenomena that affect sample representation.

Without being bound to theory, the method of the instant invention is believed to be better suited to sampling low fluid concentrations than has been found in the prior art in large part because of its ability to mitigate the effects of adsorption onto the interior surface of the sample vessel. It is well known that fluids often adsorb rather easily onto such surfaces. Generally, gases tend to adsorb with even greater specificity than do liquids. Thus, if one is seeking to analyze a particular gaseous analyte they must account for the affinity of that analyte to adsorb onto the vessel surface. Fluids can adsorb in a state of equilibrium such that volumetric uptake of the surface is held relatively constant.

This phenomenon can be quite complex and can involve any number of variables including but not limited to the composition of the analyte, composition of the vessel surface, layering and particle separation phenomena, equilibrium conditions, temperature, pressure, and other related factors. Thus, obtaining a representative sample of analyte and calculating its concentration is a particularly troublesome problem where the analyte concentration is low and it has an affinity for the vessel surface.

Again, without being bound to theory, the method of the instant invention is believed to overcome this problem by recognizing that the effect of analyte adsorption can be negated by treating the problem analogously to the manner in which one accounts for tare weight in gravimetric analysis. Here, sample is bellowsed into and out of the vessel until the vessel surface has adsorbed all of the analyte that it is capable of adsorbing. A sample is then taken from the sample environment. When the sample vessel is then emptied so that its contents can be analyzed, a more accurate proportion of analyte is found in the sample because the adsorptive capacity of the vessel surface and analyte is saturated. The vessel with saturated adsorbing analyte is analogous to the tare weight of a vessel used to weigh a sample.

Again, without being bound to theory, it is believed that filling the bag with sample invites analyte to adsorb onto the vessel surface. When the vessel is emptied the analyte is discharged back into its original environment but some of the adsorbed analyte remains adsorbed on the vessel surface. Bellowsing is repeated until the adsorptive capacity of the vessel surface is saturated. Frequently, this can be done with only one repetition of the bellowsing process. However, numerous repetitions of this process may be necessary. It has been found that analyte concentrations between about 10 ppb and about 100 ppm are easily sampled using three iterations of bellowsing. For example, samples containing concentrations of about 10 ppb of benzene have been taken after in this manner.

Collecting samples at atmospheric conditions does not require a high vacuum, but when it is necessary to rapidly collect a sample (frequently referred to as a "grab sample"), a vacuum of about 5" of Hg or more may be necessary. The ability of this device to sustain such a strong vacuum allows one to extract a soil gas sample for analysis from formations where this was previously not possible.

Samples are sometimes obtained from lines that are under higher vacuum, such as lines that carry samples to process analyzers for continuous emissions monitoring. The sample pumps for these analyzers are put on the exhaust side of the analyzer and process samples are then transported under vacuum to them. Grab samples can be obtained from these lines to the process analyzers using the methods outlined above.

There are also sampling conditions in which one must be able to sustain a high vacuum for a considerable length of time either because one is attempting to control the flow of sample to the sample vessel or the sample is slowly permeating from a trapped zone into the vessel. Collection of a time averaged sample (an integrated bag sample) is often desirable under such circumstances. The inlet valve, 11 can be left partially open to allow sample metering in this case. This can also be the case during the collection of soil gas samples for environmental remediation with a tightly packed ground formation.

This method is also amenable to sampling liquids since their behavior as fluids is similar in many respects to the behavior of gases. It has been found, for example, that many of the problems commonly encountered in sampling liquids for analyzing volatiles are overcome through the practice of this method and the use of the instant apparatus. The commonly used method of determining analyte concentration from Henry's Law provides a representative example of the advantages provided by the practice of the instant invention in its capacity to sample liquids.

As described above, liquid analytes present in a liquid medium are often analyzed by sampling a known quantity of liquid and determining two additional parameters, the temperature of the liquid sample, and the volume of air found in the headspace over the sample. If a sample can be obtained without exposure to the atmosphere a more accurate determination of the analytes present in the liquid can be achieved. Once captured, a known volume of air can be introduced over the liquid to form a headspace. Henry's Law is then applied to determine the analyte concentration in the liquid matrix as a function of the concentration of the analyte in the headspace. "TEDLAR" bags are particularly well suited as collection vessels for such an application.

ILLUSTRATIVE EXAMPLE

A 38.3 ppm $H_2S$ standard sample was obtained from the Scott Specialty Gases Company. Two aliquots were prepared from this standard for sampling by the method of the instant invention with comparison to the methods of the prior art. One aliquot consisted of a 15 ppb sample prepared by diluting 3.5 ml of the standard in nine liters of zero air (ultra high purity air). The other aliquot consisted of an undiluted sample of standard.

Three samples were withdrawn from the aliquots using the device of the instant invention. The device was bellowsed three times before each sample was captured. Captured sample was then analyzed using a GC with a photoionization detector to determine the concentration of analyte. The 15 ppb samples were all within 0.5% of the known value of the concentration with a Cv within 5%. The 40 ppm samples were all within 0.9% of the known value of the concentration with a Cv within 5%.

Three samples were also withdrawn from the aliquots using an "S-1000" syringe manufactured by the Hamilton Company. The method did not incorporate bellowsing before sample capture. The captured sample was analyzed using a GC with a photoionization detector to determine the concentration of analyte. The 15 ppb samples were analyzed as having a 12% greater concentration than what was known to be in the sample. The 40 ppm samples were analyzed as having 2.75% less than the known concentration of the sample. Cvs for both samples were also within 5%.

This example demonstrates that the method and device of the instant invention can be used to take samples which are consistently more accurate than was previously possible. While the invention has been described in detail for the purpose of illustration, it is not to be construed or limited thereby but is intended to cover all changes and modifications within the spirit and scope thereof.

I claim as my invention:

1. A fluid sample collecting apparatus comprising:
   a sealable container having an opening and a cover for sealing and unsealing said opening;
   an inlet affixed to said container, said inlet including a means for communication between the inside of said container and the environment outside said container;
   a sample vessel within said container having an orifice, said orifice being removably fixed to said inlet; and
   a means for repeatedly evacuating and pressurizing the space between said vessel and said container during the sampling of a single sample;
   wherein actuation of said means for evacuating and pressurizing the space between said vessel bellows said vessel with samples of the environment outside said container.

2. The apparatus of claim 1 wherein said means for selectively evacuating and pressurizing space between said vessel and said container bellows said vessel with sample in cycles.

3. The apparatus of claim 2 wherein means for selectively evacuating and pressurizing space between said vessel and said container comprises a crossover valve, wherein bellowsing is induced by alternately switching said crossover valve between open and closed positions.

4. The apparatus of claim 3 wherein said crossover valve is a four-way valve.

5. The apparatus of claim 2 wherein the means for selectively evacuating and pressurizing the space between said vessel and said container is a syringe so that the transition between cycles is controlled manually.

6. The apparatus of claim 2 wherein the means for selectively evacuating and pressurizing the space between said vessel and said container is a pump.

7. The apparatus of claim 6 wherein the transition between cycles occurs automatically by actuation of a control means comprising a switching means and a microprocessor, said microprocessor programmed to engage said switching means so that evacuation of said space occurs a predetermined number of times at a predetermined vacuum and said collection means fills a predetermined number of times upon actuation of said control means.

8. The apparatus of claim 6 wherein a vacuum between 0.1 and 5.0 inches of Hg is created in said container during fill cycles.

9. The apparatus of claim 2 wherein the evacuation of space between said vessel and said container occurs with substantially equal vacuum among different empty cycles.

10. A method for collecting fluid samples comprising the following steps for the collection of a given sample:
    a) placing a sample collection means within a sealable container, said collection means having a communication means attached thereto and being in communication with at least one sample environment and the interior of said collection means;

b) selectively emptying the space between the collection means and the container;

c) actuating said communication means so that said collection means is substantially filled with fluid to be samples;

d) selectively pressurizing the space between the collection means and the container;

e) actuating said communication means so that said selection means is substantially emptied of fluid to be sampled;

f) repeating steps b), c), d) and e) respectively; and then g) sealing said filled collection means.

11. The method of claim 10 wherein the transition between steps c) and d) occurs manually by actuation of a crossover valve.

12. The method of claim 10 wherein the transition between steps c) and d) occurs by engaging a syringe.

13. The method of claim 10 wherein the space between said bag and said container is selectively evacuated and pressurized by engaging a pump, said pump being in communication with said space.

14. The method of claim 13 wherein said pump is engaged by actuating a control means comprising a switching means and a microprocessor, said microprocessor programmed to engage said switching means so that evacuation of said space occurs a predetermined number of times at a predetermined vacuum and said collection means fills a predetermined number of times upon actuation of said control means.

15. The method of claim 10 wherein step f) comprises emptying cycles of substantially equal vacuum.

16. The method of claim 14 wherein a vacuum between 0.1 and 5 inches of Hg is induced during fill cycles.

17. A hand-carried portable fluid sample collecting apparatus comprising:

a sealable rigid container having an opening and a cover for sealing and unsealing said opening;

an inlet, said inlet including a means for communicating between the inside of said container and the environment outside said container;

a removable sealable sample vessel within said container, said vessel having an orifice, said orifice being removably fixed to said inlet;

a pump, said pump capable of inducing a negative or positive pressure in the space between said vessel and said container; and a control means actuating said pump and rapidly and repeatedly reversing the direction of said pump during the taking of a sample thereby inducing said vessel to be filled with fluid from the environment outside said container when the pressure inside the space between said vessel and said container is negative and emptied of its contents to said environment through said inlet when the pressure inside the space between said vessel and said container is positive.

18. The apparatus of claim 17 wherein said samples are contained in a liquid matrix.

19. The apparatus of claim 17 wherein said samples are contained in a gaseous matrix.

* * * * *